(12) United States Patent
Keen et al.

(10) Patent No.: US 7,759,492 B2
(45) Date of Patent: Jul. 20, 2010

(54) ENANTIOSELECTIVE SYNTHESIS OF 13-OXOTRICYCLO[8.2.1.0.$^{3,8}$] TRIDECA-3(8),4,6-TRIENE-5-CARBOXYLATES

(75) Inventors: Stephen Philip Keen, Ware (GB); Steven Fraser Oliver, Cambridge (GB); Gavin William Stewart, Stevenage (GB)

(73) Assignee: Merck Sharp & Dohme Limited, Hoddesdon, Hertfordshire (GB)

( * ) Notice: Subject to any disclaimer, the term of this patent is extended or adjusted under 35 U.S.C. 154(b) by 552 days.

(21) Appl. No.: 11/660,334

(22) PCT Filed: Aug. 17, 2005

(86) PCT No.: PCT/GB2005/050132

§ 371 (c)(1),
(2), (4) Date: Feb. 15, 2007

(87) PCT Pub. No.: WO2006/018663

PCT Pub. Date: Feb. 23, 2006

(65) Prior Publication Data

US 2007/0244329 A1    Oct. 18, 2007

(30) Foreign Application Priority Data

Aug. 20, 2004  (GB) .................. 0418579.9

(51) Int. Cl.
*C07D 417/06*    (2006.01)
*C07C 69/78*    (2006.01)
(52) U.S. Cl. .............. 548/150; 548/221; 549/457; 549/459; 560/101
(58) Field of Classification Search .......... None
See application file for complete search history.

(56) References Cited

FOREIGN PATENT DOCUMENTS

WO    WO 03/093264    11/2003

OTHER PUBLICATIONS

P. C. Belanger et al., "Synthesis and Stereochemistry of 11-Substituted 5,6,7,8,9,10-Hexahydro-6,9-methanobenzocyclooctenes," J. Org. Chem., vol. 47, pp. 4329-4334 (1982).
D. A. Evans et al., "Bis(imine)-Copper(II) Complexes as Chiral Lewis Acid Cayalysts for the Diels-Alder Reaction," Tetrahedron Letters, vol. 34, No. 44, pp. 7027-7030 (1993).
D. A. Evans et al., "Chiral Bis(oxazoline)copper II Complexes as Lewis Acid Catalysts for teh Enantioselective Diels-Alder Reaction," J. Am. C hem. Soc., vol. 121, pp. 7559-7573 (1999).

*Primary Examiner*—Kamal A Saeed
(74) *Attorney, Agent, or Firm*—William Krovatin; Raynard Yuro

(57) ABSTRACT

An enantioselective route to compounds of formula I is disclosed:

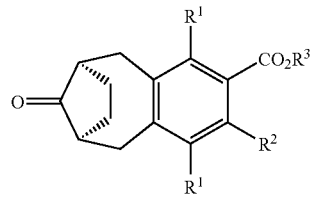

The compounds of formula I are key intermediates in the synthesis of compounds useful in treatment of Alzheimer's disease.

8 Claims, No Drawings

ENANTIOSELECTIVE SYNTHESIS OF 13-OXOTRICYCLO[8.2.1.0$^{3,8}$]TRIDECA-3(8),4,6-TRIENE-5-CARBOXYLATES

CROSS REFERENCE TO RELATED APPLICATIONS

This application is a U.S. National Phase application under 35 U.S.C. §371 of PCT Application No. PCT/GB2005/050132, filed Aug. 17, 2005, which claims priority under 35 U.S.C. §119(a) from Great Britain application no. 0418579.9, filed Aug. 20, 2004.

The present invention is in the field of synthetic organic chemistry. In particular, it provides an enantioselective synthesis of 13-oxotricyclo[8.2.1.0$^{3,8}$]trideca-3(8),4,6-triene-5-carboxylates. Such compounds are key intermediates in the synthesis of further compounds which inhibit the processing of amyloid precursor protein by gamma-secretase, and which therefore are potentially useful in the treatment or prevention of Alzheimer's disease.

WO 01/70677, WO 02/36555, WO 03/093252, WO 03/093264, WO 03/093251, WO 2004/039800, WO 2004/039370 and WO 2005/030731 disclose a variety of sulphonamide and sulphamide derivatives as gamma-secretase inhibitors. The preferred examples conform to formula (1):

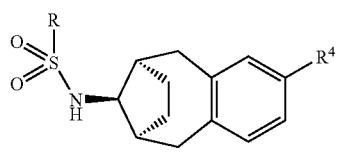

(1)

in which R$^4$ represents a variety of functional groups and R completes a Variety of sulphonamide and sulphamide moieties, including sulphamide moieties in the form of a spiro-linked 1,1-dioxo-2,3,4,5-tetrahydro-1,2,5-thiadiazole ring (as disclosed in WO 02/36555, WO 03/093252, WO 03/093264 and WO 03/093251, for example). Alkyl (1R,10S)-13-oxotricyclo[8.2.1.0$^{3,8}$]trideca-3(8),4,6-triene-5-carboxylates of formula (2a):

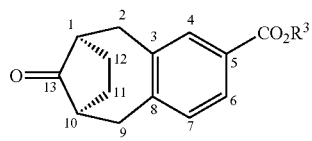

(2a)

where R$^3$ represents methyl, ethyl and the like, represent useful intermediates in the synthesis of such compounds. However, the conventional routes to esters (2a), such as those disclosed in the aforementioned PCT publications, inevitably lead to a racemic mixture of esters (2a) and their enantiomers (2b):

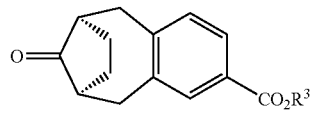

(2b)

Although these racemic mixtures have been resolved successfully, 50% of the starting materials are wasted in production of the unwanted isomer, and hence the overall efficiency of the process is low.

There is thus a need for an enantioselective synthesis of alkyl (1R,10S)-13-oxotricyclo[8.2.1.0$^{3,8}$]trideca-3(8),4,6-triene-5-carboxylates such as the compounds of formula (2a).

Evans et al describe the use of chiral bis(oxazoline)copper (II) complexes (*J. Am. Chem. Soc.*, 1999, 121, 7559-73) and chiral bis(imine)copper(II) complexes (*Tetrahedron Lett.*, 1993, 34, 2027-2030) as catalysts in enantioselective Diels-Alder reactions, but there is no disclosure or suggestion of utility in constructing a tricyclo[8.2.1.0$^{3,8}$]trideca-3(8),4,6-triene system.

According to the invention there is provided an enantioselective process for preparing a compound of formula I:

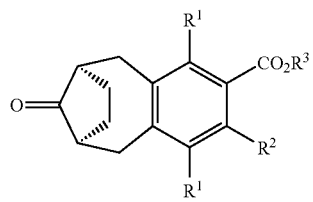

I comprising the steps of:

(a) reacting a compound of formula II

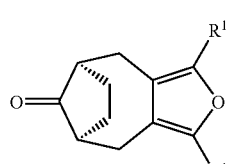

II with a compound of formula III:

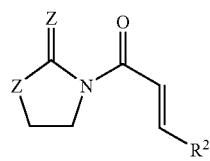

III in the presence of a catalyst selected from:

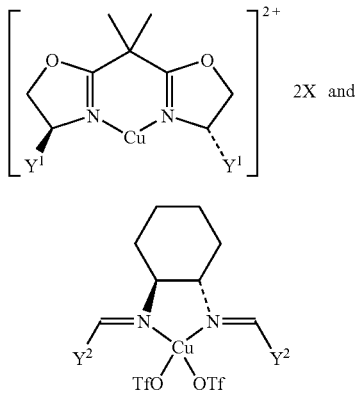

to form a compound of formula IV:

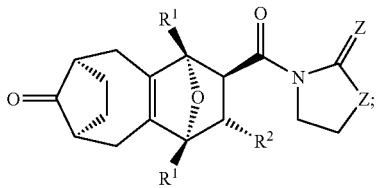

(b) treating said compound of formula IV with $R^3O^-M^+$ to form a compound of formula V:

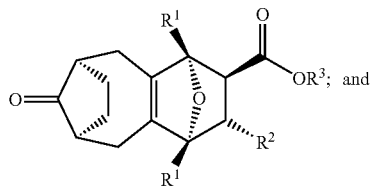

(c) dehydrating said compound of formula V to form the compound of formula I;

wherein
$R^1$ is H or $C_{1-4}$alkyl;
$R^2$ is H, $C_{1-4}$alkyl, phenyl, or Cl;
$R^3$ is $C_{1-4}$alkyl or benzyl;
Z is O or S;
M is an alkali metal;
X is $SbF_6^-$, $BF_4^-$, $PF_6^-$ or $CF_3SO_3^-$;
each $Y^1$ is t-butyl; i-propyl, phenyl or 1-naphthyl;
each $Y^2$ is t-butyl, phenyl, 4-cyanophenyl, 2-chlorophenyl, 2,6-dichlorophenyl or 2,6-difluorophenyl; and
Tf represents trifluoromethylsulfonyl.

Hereinafter, the description $[Cu((S,S)—Y^1-box)]X_2$ is used to denote the catalyst of structure A.

In formulae I-V, $R^1$ is H or $C_{1-4}$alkyl such as methyl, ethyl or propyl. Typically, $R^1$ is H or methyl, and preferably $R^1$ is H.

$R^2$ represents H, $C_{1-4}$alkyl, phenyl or Cl. Typically, $R^2$ represents H, or methyl, but preferably represents H.

$R^3$ represents benzyl or $C_{1-4}$alkyl, in particular methyl or ethyl, and most preferably methyl.

Z represents O or S. In a preferred embodiment Z represents O.

M represents an alkali metal, such as Na or K, preferably Na.

X represents $SbF_6^-$, $BF_4^-$, $PF_6^-$ or $CF_3SO_3^-$. In a preferred embodiment, X represents $SbF_6^-$.

The two $Y^1$ groups are identical and are selected from t-butyl, i-propyl, phenyl and 1-naphthyl, of which t-butyl is preferred.

Similarly, the two $Y^2$ groups are identical and are selected from t-butyl, phenyl, 4-cyanophenyl, 2-chlorophenyl, 2,6-dichlorophenyl and 2,6-difluorophenyl, of which t-butyl is preferred.

In step (a) of the inventive process, the reaction of the compound of formula II with the compound of formula III is typically carried out under an inert atmosphere (e.g. nitrogen) at reduced temperature in an aprotic solvent. The reaction is preferably carried out at a temperature below −50° C., most preferably at about −78° C. The solvent is preferably a chlorinated hydrocarbon, most preferably dichloromethane. However, if the catalyst is of Formula B, then higher temperatures (e.g. up to 0° C.) and other solvents (e.g. acetonitrile) may be used. Preferably, the compound of formula III is present in excess (e.g. 2-fold molar excess) over the compound of formula II. In a typical procedure, the compounds of formula II and III are dissolved in dichloromethane, put under a nitrogen atmosphere, cooled to −78° C., then treated with a solution of the catalyst in dichloromethane. A suitable loading of catalyst is about 10 mole % based on the compound of formula II.

A solution of catalyst A may be prepared by mixing an excess of AgX (e.g. 2-fold) with $[Cu((S,S)—Y^1-box)]$ $Cl_2.CH_2Cl_2$ in dichloromethane solution and filtering the resulting mixture (see also Evans et al, supra).

A bis(imine) catalyst solution may be prepared by mixing $Cu(OTf)_2$ with a slight excess of the appropriate cyclohexane di-imine, e.g. (1 S,2S)—N,N-bis(2,2-dimethylpropylidene) cyclohexane-1,2-diamine, (e.g. 1.1-fold) in the reaction solvent of choice (preferably dichloromethane or acetonitrile) at ambient temperature.

After addition of the catalyst, the mixture is stirred until the reaction is complete. Completion of the reaction is evidenced by disappearance of the compound of formula II, which may be monitored by conventional techniques, e.g. HPLC. Generally speaking, the reaction is complete after 20 hours' stirring at −78° C., or 3 hours at 0° C.

The resulting Diels-Alder adduct of formula IV may be isolated by any suitable method, but a preferred method involves quenching the reaction with aqueous alkali (e.g. conc. $NH_4OH$), warming to ambient temperature, dilution with water (about 1 volume), then conventional extractive work-up with dichloromethane. Evaporation of the combined extracts and crystallisation of the residue from ethyl acetate/heptane 1:2 provides the compound of formula IV, sufficiently pure for use in the next step.

In step (b) of the inventive process, the adduct of formula IV is treated with $R^3O^-M^+$ to form the ester V. This may be carried out by adding to a solution of the adduct in an aprotic solvent (such as dichloromethane) a solution of the alkoxide $R^3O^-M^+$ in $R^3OH$ (e.g. a 0.5M solution of sodium methoxide in methanol). A two-fold molar excess of the alkoxide is typically used. The addition is preferably carried out at reduced temperature, e.g. at about −60° C. with subsequent warming to 0° C. over a period of several hours. Thereafter, the ester V may be isolated by quenching the reaction mixture with about an equal volume of saturated aqueous ammonium chloride followed by conventional extractive work-up using dichloromethane. Evaporation of the dried organic extract affords the ester in a sufficiently pure state for use in the next step.

In step (c) of the inventive process, a variety of reagents may be used to effect dehydration (and hence aromatisation) of the compound of formula V. Suitable reagents include boron trihalides, ferric chloride in acetic anhydride and trifluoromethane sulfonic anhydride, of which boron trihalides (in particular, $BCl_3$) or $FeCl_3/Ac_2O$ are preferred. In a typical procedure, the compound of formula V is reacted with excess $BCl_3$ (e.g. 2-fold molar excess) in dichloromethane solution at reduced temperature (e.g. about −40° C.). After warming to ambient temperature, quenching with water, separation and evaporation of the organic layer, the residue is refluxed for about 18 hours in acetonitrile to complete the conversion to the compound of formula I. The product may be purified by conventional means, such as crystallisation or chromatography.

All three steps of the inventive process give high yields. Furthermore, step (a) proceeds with a high degree of stereoselectivity, giving the desired Diels Alder adduct in greater than 99% diastereomeric and enantiomeric excess. Consequently, the compound of formula I is ultimately obtained essentially free from the undesired (1S,10R)-isomers.

The compounds of formula II, formula IV and formula V as defined above are believed to be novel, and individually constitute further aspects of the invention.

Compounds of formula II may be obtained by routes which are analogous to published routes for the construction of bicyclo[4.2.1]non-3-en-9-one ring systems, (e.g. Iddon et al, *J. Chem. Soc. Perkins Trans.* 1, 1990, 1083-90; Bélanger et al, *J. Org. Chem.*, 1982, 47, 4329-34). Thus, bis(halomethyl) furans (VI) are refluxed in acetonitrile with enamines VII in the presence of base:

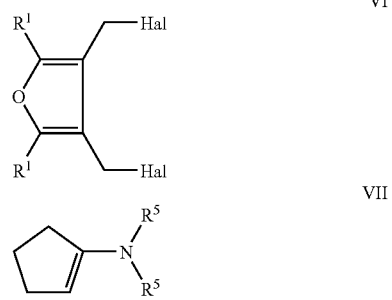

where Hal represents Br or Cl, the $R^5$ groups complete a heterocyclic ring, and $R^1$ has the same meaning as before. When Hal is Cl, addition of a catalytic amount of sodium iodide is beneficial. Hydrolysis of the resulting iminium salts then provides the desired tricyclic furans II. The base is suitably a trialkylamine such as triethylamine or diisopropylethylamine, and the $R^5$ groups typically complete a ring of 5 or 6 members, such as pyrrolidine, piperidine or morpholine.

Detailed procedures are provided in the Examples section herein.

The compounds of formula I are versatile intermediates for the synthesis of sulphonamides and sulphamides having activity as inhibitors of gamma-secretase, as described in WO 01/70677, WO 02/36555, WO 03/093252, WO 03/093264, WO 03/093251, WO 2004/039800, WO 2004/039370 and WO 2005/030731, the disclosure of which is incorporated herein by reference. The ketone group in the compounds of formula I may be transformed into a variety of sulphonamide and sulphamide functionalities as described in the above-listed published applications, including spiro-linked cyclic sulphamide moieties as disclosed in WO 02/36555, WO 03/093252, WO 03/093264, WO 03/093251, WO 2004/039800 and WO 2005/030731. Likewise, the ester group —$CO_2R^3$ in the compounds of formula I may be converted into a variety of different functionalities, as disclosed in the above-listed published applications. In particular, the ester group serves as the precursor for a variety of 5-membered heteroaryl substituents, as disclosed in WO 03/093252, most notably a 5-aryl-1-alkylpyrazol-3-yl substituent.

Most preferably, the ketone group is further elaborated into a 3,3-spiro-linked 5-substituted-2,3,4,5-tetrahydro-1,2,5-thiadiazole-1,1-dioxide ring where the 5-substituent is $C_{1-6}$alkyl or $C_{2-6}$alkenyl optionally substituted with up to 3 halogen atoms, in particular 2,2,2-trifluoroethyl. Most preferably the ester group $CO_2R^3$ is further elaborated into a 5-aryl-1-methylpyrazol-3-yl substituent, where "aryl" refers to mono-, di- or trihalophenyl, in particular 4-fluorophenyl, 4-chlorophenyl, 3,4-difluorophenyl or 3,4-dichlorophenyl, preferably 4-fluorophenyl. Suitable procedures for these transformations are disclosed in WO 03/093252, the disclosure of which is incorporated herein by reference.

The invention is illustrated by the following examples.

EXAMPLES

Example 1

5-oxatricyclo[7.2.1.0$^{3,7}$]dodeca-3,6-dien-12-one (II, $R^1$=H)

To a stirred solution of 4-(1-cyclopenten-1-yl)morpholine (10.5 g, 68.8 mmol) and N,N-diisopropylethylamine (12.0 mL, 69.0 mmol) in acetonitrile (120 mL) was added solid 3,4-bis(bromomethyl)furan (17.3 g, 68.1 mmol). The resulting solution was left to stir at rt for 15 h, by which point a yellow slurry had formed. The slurry was filtered, washing the wet-cake with acetonitrile (2×5 mL), then the resulting solid was suspended in acetonitrile (100 mL), heated to reflux, and the reaction mixture stirred at this temperature for 31 h. After cooling to ambient temperature, the resulting slurry was filtered to afford the iminium salt:

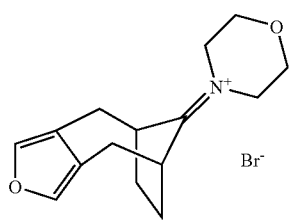

as a beige solid (9.21 g, 41%).

This salt (6.00 g, 18.4 mmol) was partially dissolved in water (30 mL) and the resulting mixture left to stir at ambient temperature for 25 h. The slurry was filtered, washing the wet-cake with water (2×5 mL), and the resulting solid was dried under vacuum to afford title compound (2.97 g, 92%) as a beige solid. If required, this material can be purified via recrystallization from methanol-water (6 and 12 mL/g, respectively) with 86% recovery: $^1$H NMR (250 MHz, CD$_2$Cl$_2$) δ 7.31-7.28 (m, 2H), 2.75 (dd, J=14.8, 5.7 Hz, 2H), 2.61-2.48 (m, 2H), 2.47 (d, J=15.1 Hz, 2H), 2.10-1.85 (m, 2H), 1.55-1.41 (m, 2H); $^{13}$C NMR (63 MHz, CD$_2$Cl$_2$) δ 225.0, 141.8, 121.8, 45.9, 27.8, 23.6.

Example 2

Diels-Alder reaction of 5-oxatricyclo[7.2.1.0$^{3,7}$] dodeca-3,6-dien-12-one

[Cu((S,S)-tert-Bu-box)]Cl$_2$.CH$_2$Cl$_2$ (0.43 g, 0.83 mmol), silver hexafluoroantimonate (0.56 g, 1.63 mmol) and dichloromethane (DCM) (15 mL) were mixed under a nitrogen atmosphere and stirred for 4 h in the dark.

Solid 5-oxatricyclo[7.2.1.0$^{3,7}$]dodeca-3,6-dien-12-one (Example 1) (2.91 g, 16.5 mmol) and 3-acryloyloxazolidin-2-one (4.66 g, 33.0 mmol) were charged to an oven-dried flask. The flask was degassed, put under a nitrogen atmosphere and then DCM (25 mL) was added and the stirred reaction mixture was cooled to −78° C. The green catalyst solution, prepared above, was then filtered through a 0.45 μm filter into the reaction mixture over ~15 min, washing the filter through with DCM (5 mL). The resulting batch was then left to stir at −78° C. for 20 h. The reaction was quenched by addition of conc. NH$_4$OH (5 mL) and allowed to warm to ambient temperature. The resulting biphasic mixture was diluted with water (50 mL) and then extracted with DCM (3×50 mL). The combined organic layers were washed with saturated brine (50 mL), dried (Na$_2$SO$_4$) and then concentrated in vacuo. The semi-solid residue obtained was taken up in EtOAc (50 mL), then heptane (100 mL) was slowly added to the resulting stirred slurry. After aging for 2 h at rt, the solid was collected by filtration and washed with 3:1 heptane-EtOAc (20 mL). After drying under vacuum, the Diels-Alder adduct IV (R$^1$=R$^2$=H, Z=O) was isolated as an off-white solid (4.74 g, 90%, >99% ee): $^1$H NMR (250 MHz, CD$_2$Cl$_2$) δ 4.99 (d, J=4.5 Hz, 1H), 4.73 (d, J=4.5 Hz, 1H), 4.39 (t, J=8.0 Hz, 2H), 4.05 (app dt, J=8.7, 4.3 Hz, 1H), 3.99-3.82 (m, 2M), 2.60-2.39 (m, 2H), 2.37-2.02 (m, 5H), 1.95 (dddd, J=11.1, 8.8, 4.5, 1.0 Hz, 1H), 1.83-1.60 (m, 4H); $^{13}$C NMR (63 MHz, CD$_2$Cl$_2$) δ 222.4, 171.3, 154.0, 141.7, 135.7, 85.1, 84.9, 62.9, 45.6, 45.5, 45.4, 43.3, 31.8, 30.2, 29.2, 26.9, 26.3.

Alternative Procedure (+)-1,2-trans-Diaminocyclohexane (250 mg, 2.18 mmol) in CH$_2$Cl$_2$ (20 mL) was treated with Na$_2$SO$_4$ (923 mg, 6.50 mmol) and trimethylacetaldehyde (473 μL, 4.35 mmol). The mixture was stirred at ambient temperature under an atmosphere of N$_2$ for 0.5 h then filtered. The filter was washed with CH$_2$Cl$_2$ (5 mL) and the combined organics were evaporated to give N,N'-bis-(2,2-dimethylpropylidene)-cyclohexane-1,2-diamine (610 mg, 98%) as an off-white semi solid.

$^1$H NMR (400 MHz, CD$_2$Cl$_2$) δ 7.45 (s, 2H), 3.07 (m, 2H), 1.74 (m, 2H), 1.59 (m, 4H), 1.37 (m, 2), 1.00 (s, 18H); $^{13}$C NMR (100 MHz, CD$_2$Cl$_2$) δ 170.5, 73.7, 35.7, 33.2, 26.9, 24.5.

N,N'-Bis-(2,2-dimethylpropylidene)-cyclohexane-1,2-diamine (78 mg, 0.312 mmol) and Cu(OTf)$_2$ (103 mg, 0.284 mmol) were mixed at ambient temperature in anhydrous acetonitrile (1.5 mL) for 0.5 h under a nitrogen atmosphere. The resulting deep green solution was cooled to 0° C. and treated with a mixture of 5-oxatricyclo[7.2.1.0$^{3,7}$]dodeca-3, 6-dien-12-one (500 mg, 2.84 mmol) and 3-acryloyloxazolidin-2-one (801 mg, 5.68 mmol) in acetonitrile (3 mL), added dropwise over 3 min. The resulting deep blue solution was aged at 0° C. for 2.5 h then treated with concentrated ammonium hydroxide and aged at 0° C. for 10 min. The mixture was diluted with CH$_2$Cl$_2$ (10 mL) and H$_2$O (10 mL) and the layers were separated. The aqueous phase was extracted into CH$_2$Cl$_2$ (2×10 mL) and the combined organics were dried (Na$_2$SO$_4$) and evaporated to dryness. LC analysis of the residue indicated an assay yield of 85%, endo:exo ratio of 20:1 and an endo ee of 86%. Isolation of the Diels-Alder adduct was then carried out as described previously.

Example 3

Methyl (1R,10S)-13-oxotricyclo[8.2.1.0$^{3,8}$]trideca-3 (8),4,6-triene-5-carboxylate (I, R$^1$=R$^2$=H, R$^3$=Me)

A stirred solution the product of Example 2 (4.15 g, 13.1 mmol) in DCM (200 mL) was cooled to −60° C. under a nitrogen atmosphere. A 0.5 M solution of sodium methoxide in methanol (52 mL, 26 mmol) was slowly added over 30 min., then the reaction mixture was allowed to warm to 0° C. over a period of 4 h. At this point, HPLC analysis indicated that the reaction was complete (<1% starting material remained). The cooling bath was removed and the resulting solution allowed to warm to ambient temperature. The reaction was quenched by addition of saturated aqueous NH$_4$Cl (200 mL) and the two layers were separated. The aqueous phase was extracted with DCM (150 mL), and the combined organic layers were washed with half-saturated brine (2×100 mL) and then dried (Na$_2$SO$_4$). Concentrating in vacuo afforded methyl ester V (R$^1$=R$^2$=H, R$^3$=Me) as a beige solid (3.15 g, 92%): $^1$H NMR (250 MHz, CD$_2$Cl$_2$) δ 4.81 (d, J=4.7 Hz, 1H), 4.68 (d, J=4.6 Hz, 1H), 3.59 (s, 3H), 3.07 (app dt, J=9.0, 4.5 Hz, 1H), 2.59-2.44 (m, 2H), 2.41-1.84 (m, 7H), 1.73-1.63 (m, 2H), 1.56 (dd, J=11.4, 4.0 Hz, 1H).

A stirred solution of this intermediate (94 mg, 0.36 mmol) in DCM (10 ml) was cooled to −40° C. and a 1 M solution of boron trichloride in DCM (0.72 mL, 0.72 mmol) was then added dropwise. The resulting mixture was allowed to warm to ambient temperature over 4 h and then aged a further 1 h. HPLC analysis showed that starting material had been completely consumed by this point. Therefore, the reaction was quenched by addition of water (10 mL) and the two layers were separated. The organic layer was dried (Na$_2$SO$_4$) and then concentrated in vacuo. The residue obtained was dissolved in acetonitrile (10 mL) and the resulting solution was heated to 80° C. After stirring at this temperature for 18 h, the solution was cooled to ambient temperature and then concentrated to dryness. Purification of this crude product by flash column chromatography (3:1 hexane/MTBE) afforded the title compound as a white solid (68 mg, 78%, 99% ee): $^1$H NMR (250 MHz, CD$_2$Cl$_2$) δ 7.88 (s, 1H), 7.84 (dd, J=8.1, 1.5 Hz, 1H), 7.30 (d, J=7.6 Hz, 1H), 3.88 (s, 3H), 3.06 (ddd, J=15.5, 7.9, 2.1 Hz, 2H), 2.87 (d, J=15.4 Hz, 2H), 2.62-2.52 (m, 2H), 1.93-1.82 (m, 2H), 1.32-1.15 (m, 2H).

The invention claimed is:

1. An enantioselective process for preparing a compound of formula I:

I comprising the steps of:
(a) reacting a compound of formula II

II with a compound of formula III:

III in the presence of a catalyst selected from:

A 2X and

B to form a compound of formula IV:

IV (b) treating said compound of formula IV with $R^3O^-M^+$ to form a compound of formula V:

V (c) dehydrating said compound of formula V to form the compound of formula I;

wherein
$R^1$ is H or $C_{1-4}$alkyl;
$R^2$ is H, $C_{1-4}$alkyl, phenyl, or Cl;
$R^3$ is $C_{1-4}$alkyl or benzyl;
Z is O or S;
M is an alkali metal;
X is $SbF_6^-$, $BF_4^-$, $PF_6^-$ or $CF_3SO_3^-$;
each $Y^1$ is t-butyl; i-propyl, phenyl or 1-naphthyl;
each $Y^2$ is t-butyl, phenyl, 4-cyanophenyl, 2-chlorophenyl, 2,6-dichlorophenyl or 2,6-difluorophenyl; and
Tf represents trifluoromethylsulfonyl.

2. A process according to claim 1 in which the catalyst in step (a) is of formula A.

3. The process of claim 2 in which $Y^1$ represents t-butyl and X represents $SbF_6^-$.

4. A process according to claim 1 in which the catalyst in step (a) is of formula B and $Y^2$ represents t-butyl.

5. The process of claim 4 in which step (a) is carried out in acetonitrile at 0° C. or below.

6. A process of claim 1 in which $R^1$ and $R^2$ are both H.

7. A process of claim 1 in which Z is O.

8. A process of claim 1 in which the dehydration in step (c) is effected using $BCl_3$ or using ferric chloride and acetic anhydride.

* * * * *